(12) United States Patent
Everingham et al.

(10) Patent No.: US 12,180,449 B2
(45) Date of Patent: Dec. 31, 2024

(54) SELF-CONTAINED MOLD FOR CULTURE AND TRANSPORT OF 3D CELLULAR GELS

(71) Applicant: Boise State University, Boise, ID (US)

(72) Inventors: John Everingham, Boise, ID (US); Trevor Lujan, Boise, ID (US)

(73) Assignee: Boise State University, Boise, ID (US)

( * ) Notice: Subject to any disclaimer, the term of this patent is extended or adjusted under 35 U.S.C. 154(b) by 754 days.

(21) Appl. No.: 16/284,449

(22) Filed: Feb. 25, 2019

(65) Prior Publication Data

US 2019/0309247 A1    Oct. 10, 2019

Related U.S. Application Data

(60) Provisional application No. 62/653,986, filed on Apr. 6, 2018.

(51) Int. Cl.
*C12M 1/00* (2006.01)
*B01L 3/00* (2006.01)
(Continued)

(52) U.S. Cl.
CPC ....... *C12M 23/34* (2013.01); *B01L 3/502707* (2013.01); *B01L 3/505* (2013.01);
(Continued)

(58) Field of Classification Search
CPC ... B01L 3/502707; B01L 3/505; C12M 21/08; C12M 23/02; C12M 23/34; C12M 25/14;
(Continued)

(56) References Cited

U.S. PATENT DOCUMENTS 7,303,715 B1 * 12/2007 Fox .................. B29C 39/26
264/219
7,713,734 B2    5/2010 Ghosh et al.
(Continued)

OTHER PUBLICATIONS

Screen captures from YouTube video clip entitled "SPL Cell Culture Slide & Hybridwell," 4 pages, uploaded on Sep. 19, 2016 by user "SPL Life Sciences". Retrieved from internet:<https://www.youtube.com/watch?v=8qYCPFDrmWQ> (Year: 2016).*
(Continued)

*Primary Examiner* — Lydia Edwards
(74) *Attorney, Agent, or Firm* — McKee, Voorhees & Sease, PLC (57) ABSTRACT

A mold capable of preparing a cellular or acellular construct includes a block including a three-dimensional cavity for a sample, a base, and a removable sheet inserted between the block and the base. The sheet may be coated with silicone grease prior to insertion of the sheet between the block and the base. Mechanical constraints may be included at each end of the cavity to constrain cell driven contraction and to allow for gripping the sample after the sample is removed from the mold. The sample may be prepared by partially filling the cavity with gel, filling the remaining portion of the cavity with culture media, and allowing a three-dimensional sample to culture within the cavity for a time. The sample may be transported to a bioreactor and ejected from the mold by removing the sheet and applying pressure to the mechanical constraints.

19 Claims, 5 Drawing Sheets

(51) Int. Cl.
*C12M 3/00* (2006.01)
*C12N 5/00* (2006.01)

(52) U.S. Cl.
CPC ............ *C12M 21/08* (2013.01); *C12N 5/0068* (2013.01); *C12N 2527/00* (2013.01); *C12N 2533/40* (2013.01); *C12N 2535/00* (2013.01); *C12N 2539/00* (2013.01)

(58) Field of Classification Search
CPC ............ C12N 2527/00; C12N 2533/40; C12N 2535/00; C12N 2539/00; C12N 5/0068
See application file for complete search history.

(56) References Cited

U.S. PATENT DOCUMENTS

| | | |
|---|---|---|
| 8,501,476 B2 | 8/2013 | Morgan et al. |
| 9,274,101 B2 | 3/2016 | Bochner et al. |
| 9,422,524 B2 | 8/2016 | Van Apeldoorn et al. |
| 9,751,084 B2 | 9/2017 | Greenizen et al. |
| 2016/0297131 A1 | 10/2016 | Kameoka et al. |
| 2017/0211044 A1 | 7/2017 | Huebsch et al. |
| 2017/0283757 A1 | 10/2017 | Carter et al. |
| 2017/0362588 A1 | 12/2017 | Sheinman et al. |

OTHER PUBLICATIONS

Cell Culture Slide I. Technical Data Sheet [online], SPL Life Sciences, 1998 [retrieved on Dec. 1, 2022]. Retrieved from the Internet:<http://www.spllifesciences.com/en/m21.php?cate=1&idx=252>. (Year: 2018).*

Kenoian et al., "Design of Device to Stretch Tunable Stiffness Substrates for Cell Studies", Major Qualifying Project Submitted to the faculty of WPI, 79 pages, Apr. 30, 2009.

* cited by examiner

SELF-CONTAINED MOLD FOR CULTURE AND TRANSPORT OF 3D CELLULAR GELS

CROSS-REFERENCE TO RELATED APPLICATIONS

This application claims priority under 35 U.S.C. § 119 to provisional patent application U.S. Ser. No. 62/653,986, filed Apr. 6, 2018. The provisional patent application is herein incorporated by reference in its entirety, including without limitation, the specification, claims, and abstract, as well as any figures, tables, appendices, or drawings thereof.

GRANT REFERENCE

This invention was made with government support under U.S. National Institute of General Medical Sciences research grant number P20GM109095. The government has certain rights in the invention.

FIELD OF THE INVENTION

The present invention relates generally to laboratory made 3D tissue surrogates seeded with cells that are molded into specific shapes so that the 3D tissue surrogates can be mechanically stretched or compressed. More particularly, but not exclusively, the present invention relates to a method and device for providing an innovative mold to create these cellular gels.

BACKGROUND OF THE INVENTION

The background description provided herein is for the purpose of generally presenting the context of the present disclosure. Work of the presently named inventors, to the extent the work is described in the present disclosure, as well as aspects of the description that may not otherwise qualify as prior art at the time of filing, are neither expressly nor impliedly admitted as prior art.

Mechanobiology is a field of science that focuses on how cells respond to physical forces. The process by which cells convert mechanical stimuli to biomechanical activity is known as mechanotransduction. The process of mechanotransduction and matrix remodeling is observed in many different musculoskeletal tissues including bone, ligament, muscle, and tendon. Mechanical loading can increase the size and strength of musculoskeletal tissues while the absence of load can cause the tissue structure to become weak.

The response of cells to mechanical and chemical stimulation has largely been studied using in-vitro (performed outside a living organism) cell culture systems. For the modeling of musculoskeletal tissue, cells are often seeded within a matrix made of gelatinized collagen, fibrin, or agarose to create a surrogate tissue. For the cells to remain alive, the surrogate tissue is placed within a device called a cell culture incubator that stimulates the environmental conditions within the body. Additionally, the surrogates must be submerged in a fluid called cell culture media to provide nutrients to the cells and prevent growth of bacteria that kills the cells. These surrogate tissues are often mechanically stimulated (stretched/compressed) while within an incubator using devices called bioreactors. The strength and structural composition of the surrogates can be measured before and after tissue culture to determine how cells respond to the external stimuli being applied during culture. These tissue surrogates provide an effective experimental tool to understand the physical effects of mechanical stimuli on cells in a 3D environment, but these tissue surrogates do not have the same level of structural and compositional complexity, nor do these tissue surrogates have the mechanical strength of actual tissue.

When creating these tissue surrogates the gel starts as a liquid with cells mixed homogenously throughout. The liquid is often poured into a petri dish where the liquid will often stiffen and gelatinize over a period of a few days. To apply mechanical stimulation to the samples, the samples need to be cut into specific shapes after gelation or molded before the samples are gelatinized. Many cells are wasted when the gels are cut into shapes because the cells are mixed homogenously throughout the gel. Thus, molds have been utilized as an effective way to reduce material waste.

Current molds for the gels are made of bio-inert materials such as polytetrafluoroethylene (PTFE) or silicone and are placed in the bottom of a petri dish and sealed using silicone grease to prevent the liquid from spilling from the bottom of the mold. The molds are then covered with cell culture media. To transport the sample to the bioreactor, the entire petri dish needs to be moved and the sample has to be removed from the mold with tweezers. After only a few days of culture, the tissue surrogates are still very fragile which makes transport and extraction with tweezers difficult and the risk of damaging the sample high. Thus, there exists a need to create devices that allow easier transport and extraction of the tissue surrogates during the early stages of cell culture.

SUMMARY OF THE INVENTION

Therefore, it is a primary object, feature, or advantage of the present invention to improve on or overcome the deficiencies in the art.

It is another object, feature, and/or advantage of the invention to prepare a sample that is usable without a petri dish.

It is another object, feature, and/or advantage of the invention to provide a mold and a method for preparing a cellular or acellular construct that uses less cell culture media than established methods known in the art.

It is another object, feature, and/or advantage of the invention to provide a device that allows the sample to be ejected from the mold by removing the base.

It is another object, feature, and/or advantage of the invention to provide a mold designed to adapt to any three-dimensional sample geometries with planar extruded surfaces.

It is another object, feature, and/or advantage of the invention to provide a mold that is durable.

It is another object, feature, and/or advantage of the invention to provide a mold that is easily used, manufactured, repaired, and stored when not in use.

It is another object, feature, and/or advantage of the invention to provide a mold that is aesthetically pleasing.

It is another object, feature, and/or advantage of the invention to provide a device that is cost effective.

It is still yet a further object, feature, or advantage of the present invention to incorporate the mold into a system accomplishing some or all of the previously stated objectives.

The following provides a list of aspects or embodiments disclosed herein and does not limit the overall disclosure. It is contemplated that any of the embodiments disclosed herein can be combined with other embodiments, either in full or partially, as would be understood from reading the disclosure.

According to some aspects of the disclosure, a mold is capable of preparing a sample for mechanical evaluation and stimulation. The mold comprises a block including a three-dimensional cavity for a sample, a base, and a removable sheet inserted between the block and the base. The block may be made from polytetrafluoroethylene (PTFE). The base may be made from poly lactic acid (PLA). The sheet may be made from polytetrafluoroethylene (PTFE), may be thinner than the base, and may be coated with silicone grease prior to insertion of the sheet between the block and the base. The cavity may have a dog-bone geometry. The block may have a block height of twenty millimeters, a block width of thirty-three millimeters, and a block length of fifty-seven millimeters. The base may have a base width identical to the block width, a base length identical to the block length, and a base height of one and a half millimeters. The base may include a rectangular cut-out and a rectangular ridge supporting the removable sheet. The rectangular ridge may have a rectangular ridge height of one millimeter and each side of the rectangular ridge is at least one millimeter in width. The cavity may have a sample width of seven millimeters and a gauge length of twenty-one millimeters. Mechanical constraints may be included at each end of the cavity to constrain cell driven contraction and to allow for gripping the sample after the sample is removed from the mold.

According to other aspects of the disclosure, a method for preparing a sample for mechanical evaluation and stimulation includes providing the above mold, partially filling the cavity with gel, filling the remaining portion of the cavity with culture media, and allowing a three-dimensional sample to culture within the cavity for a time. The method may also include ejecting the sample from the mold by removing the sheet and applying pressure to the mechanical constraints and transporting the sample to a bioreactor for mechanical evaluation and stimulation. The culture time may comprise from one to twenty-eight days. The step of partially filling the cavity may comprise filling the cavity up to forty percent of the height of the cavity.

These or other objects, features, and advantages of the present invention will be apparent to those skilled in the art after reviewing the following detailed description of the illustrated embodiments, accompanied by the attached drawings.

BRIEF DESCRIPTION OF THE DRAWINGS

FIGS. 3A-D show an improved mold design wherein the mold is entirely self-contained. More particularly.

FIGS. 4A-C show PTFE molds for collagen gel culture. More particularly.

Various embodiments of the present disclosure illustrate several ways in which the present invention may be practiced. These embodiments will be described in detail with reference to the drawings, wherein like reference numerals represent like parts throughout the several views. Reference to specific embodiments does not limit the scope of the present disclosure and the drawings represented herein are presented for exemplary purposes.

DETAILED DESCRIPTION OF THE PREFERRED EMBODIMENTS

The following definitions and introductory matters are provided to facilitate an understanding of the present invention. Unless defined otherwise, all technical and scientific terms used herein have the same meaning as commonly understood by one of ordinary skill in the art to which embodiments of the present invention pertain.

The terms "a," "an," and "the" include plural referents unless context clearly indicates otherwise. Similarly, the word "or" is intended to include "and" unless context clearly indicate otherwise. The word "or" means any one member of a particular list and also includes any combination of members of that list.

The terms "invention" or "present invention" as used herein are not intended to refer to any single embodiment of the particular invention but encompass all possible embodiments as described in the specification and the claims.

The term "about" as used herein refers to variation in the numerical quantities that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The claims include equivalents to the quantities whether or not modified by the term "about."

The term "configured" describes an apparatus, system, or other structure that is constructed to perform or capable of performing a particular task or to adopt a particular configuration. The term "configured" can be used interchangeably with other similar phrases such as constructed, arranged, adapted, manufactured, and the like.

For purposes of the present disclosure, the term "entirely self-contained" is defined as being free from permanent external mechanical constraints. For example, a mold that is entirely self-contained may be used (and reused) without a petri dish, base plate, or a test tube. Other definitions of similar terms will be apparent to those skilled in the art after reading the entirety of the present disclosure.

Terms such as first, second, vertical, horizontal, top, bottom, upper, lower, front, rear, end, sides, concave, convex, and the like, are referenced according to the views presented. These terms are used only for purposes of description and are not limiting unless these terms are expressly included in the claims. Orientation of an object or a combination of objects may change without departing from the scope of the invention.

The apparatuses, systems, and methods of the present invention may comprise, consist essentially of, or consist of the components of the present invention described herein. The term "consisting essentially of" means that the apparatuses, systems, and methods may include additional components or steps, but only if the additional components or steps do not materially alter the basic and novel characteristics of the claimed apparatuses, systems, and methods.

The following embodiments are described in sufficient detail to enable those skilled in the art to practice the invention however other embodiments may be utilized. Mechanical, procedural, and other changes may be made without departing from the spirit and scope of the invention. Accordingly, the scope of the invention is defined only by the appended claims, along with the full scope of equivalents to which such claims are entitled.

Figure 1:
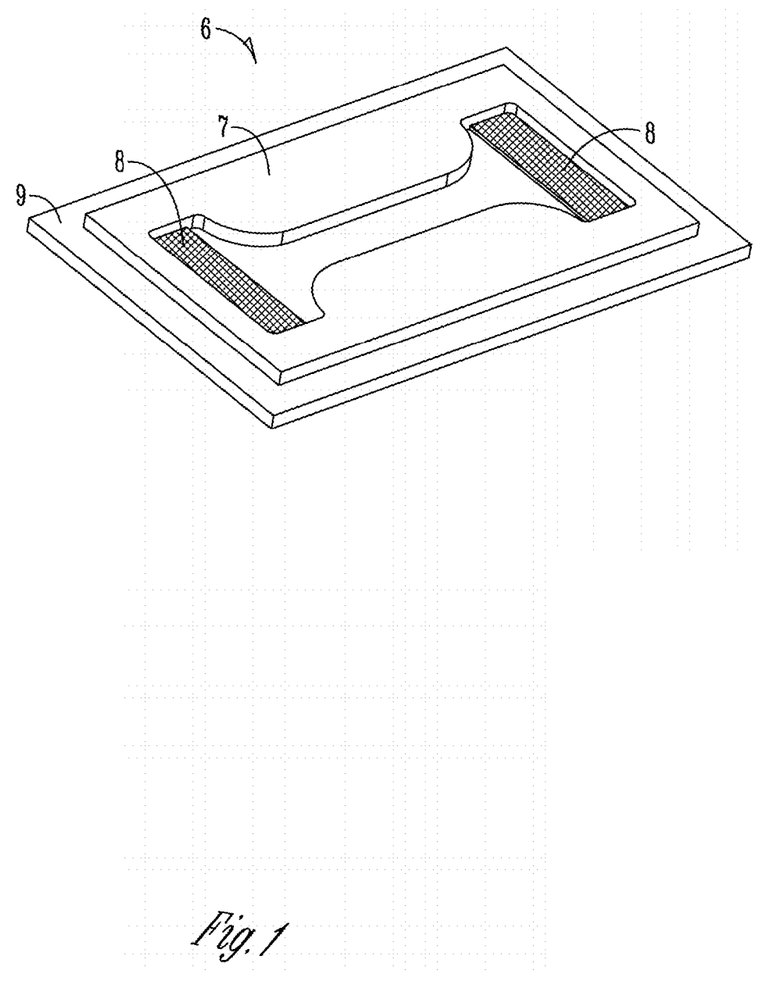
FIG. 1 shows a perspective view of a standard silicone mold for a dog-bone shaped collagen gel tissue.

FIG. 1 shows a perspective view of a standard silicone mold 6 for a dog-bone shaped collagen gel tissue. As is shown, the standard silicone mold 6 includes a silicone gasket 7, a polypropylene mesh 8, and a glass plate 9.

Figure 2:
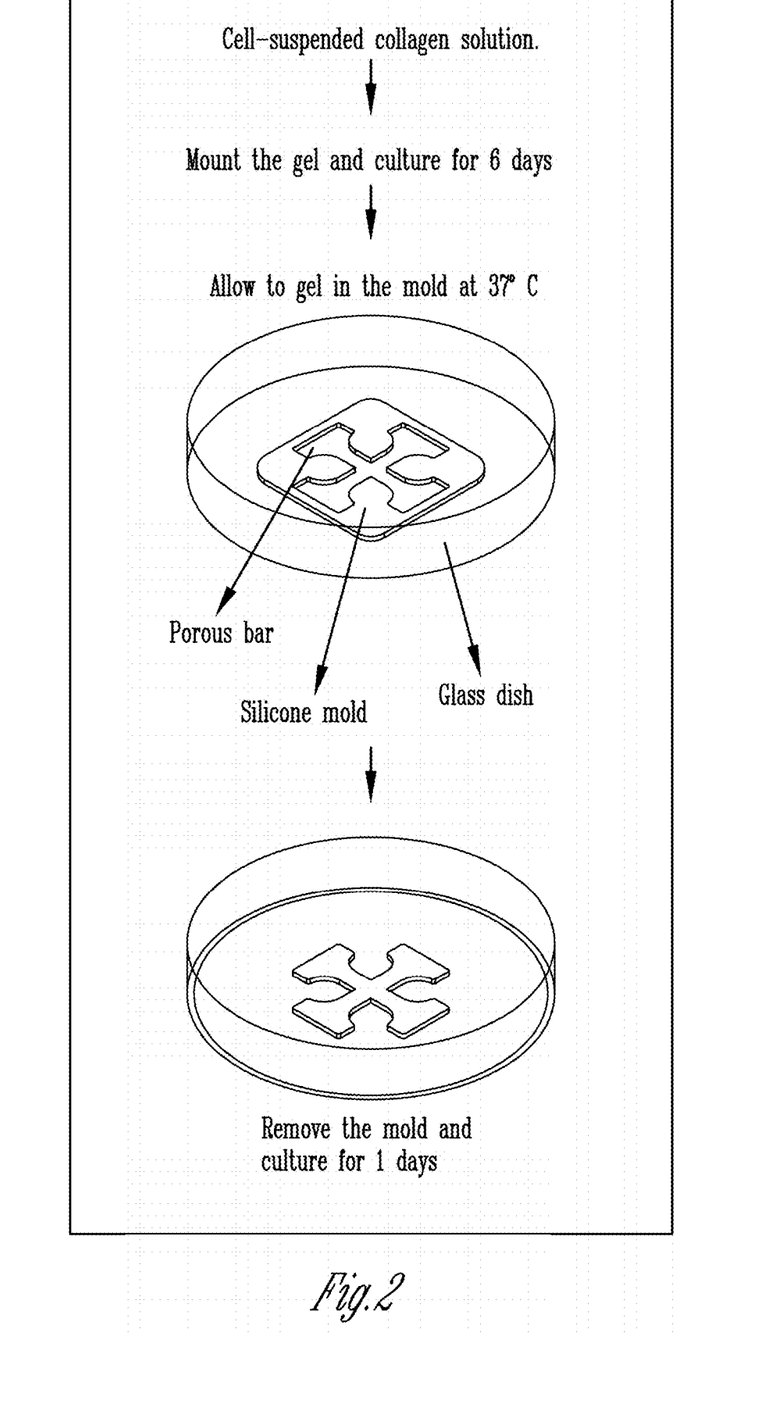
FIG. 2 shows steps for and various illustrations related to preparing a standard silicone mold for a biaxial cellular collagen gel tissue surrogate.
Figure 3A:
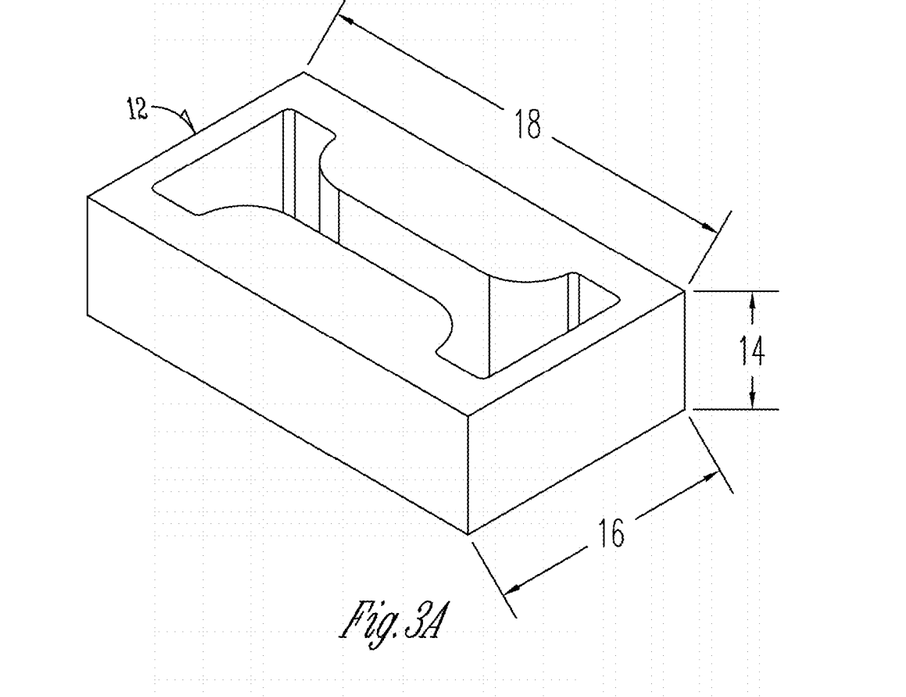
FIG. 3A shows a perspective view of a machined PTFE block.
Figure 3B:
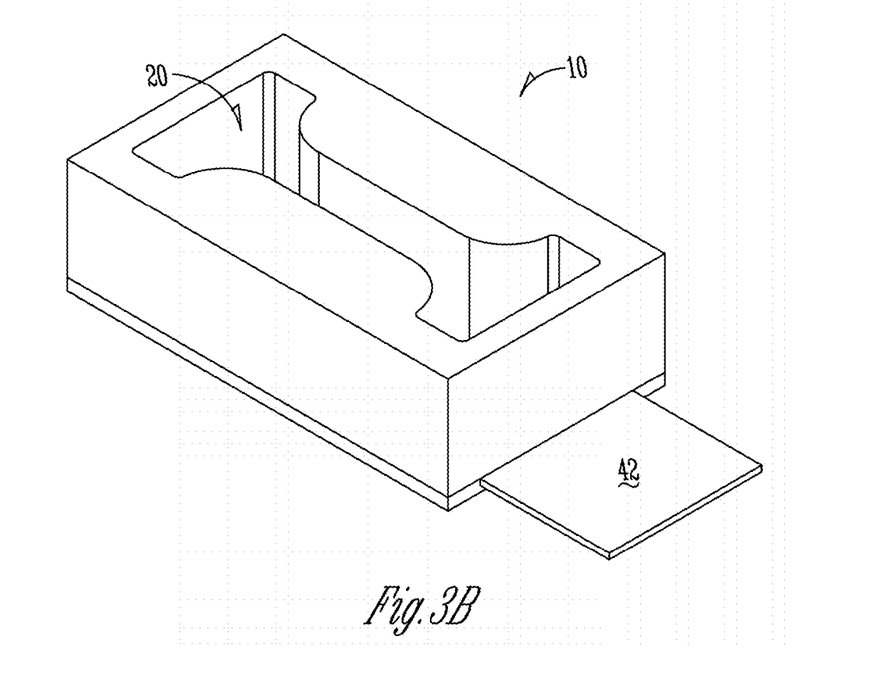
FIG. 3B illustrates a removable PTFE sheet being inserted between the machined PTFE block and a PLA base.
Figure 3C:
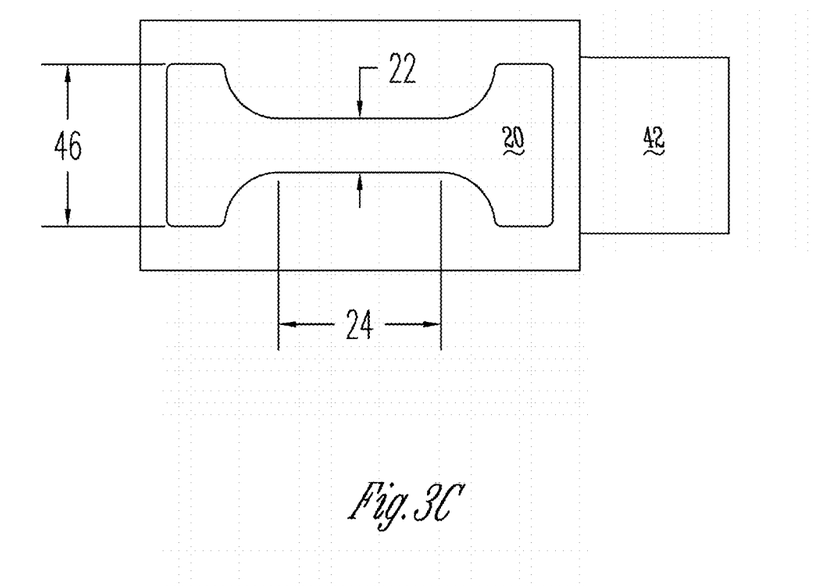
FIG. 3C shows a top elevation view of the machined PTFE block.
Figure 3D:
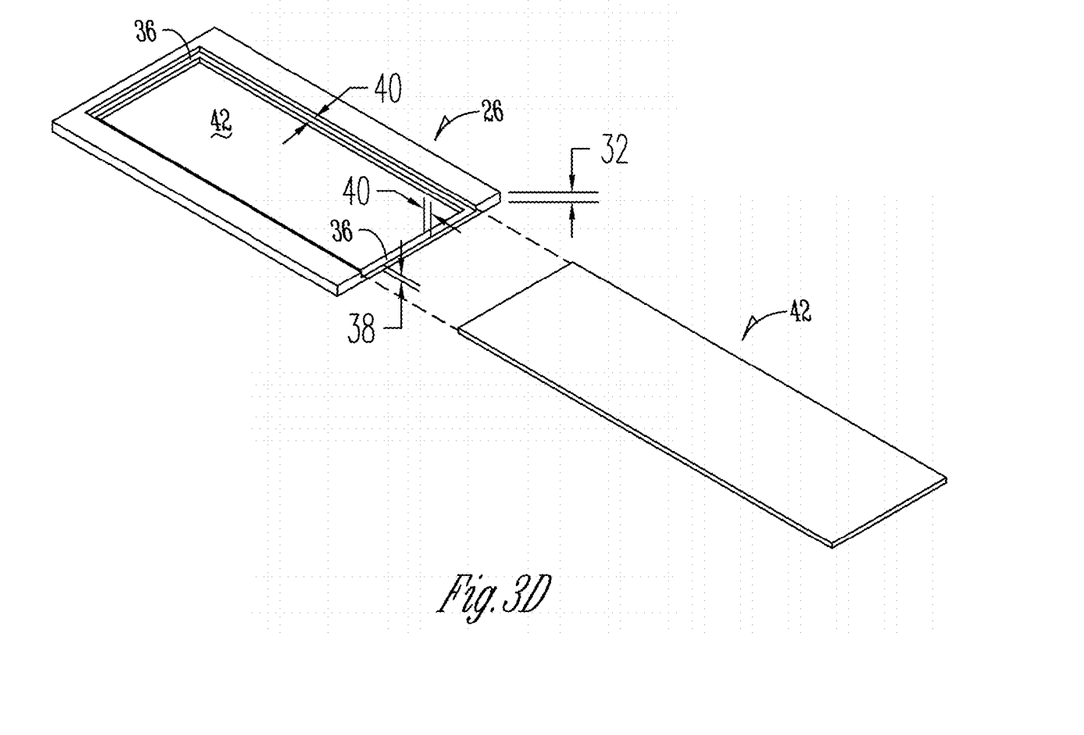
FIG. 3D shows the removable PTFE sheet alongside the PLA base.
Figure 4A:
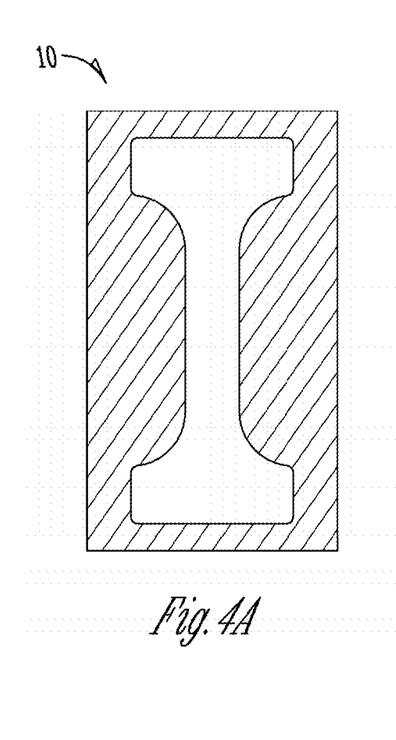
FIG. 4A shows an empty mold.
Figure 4B:
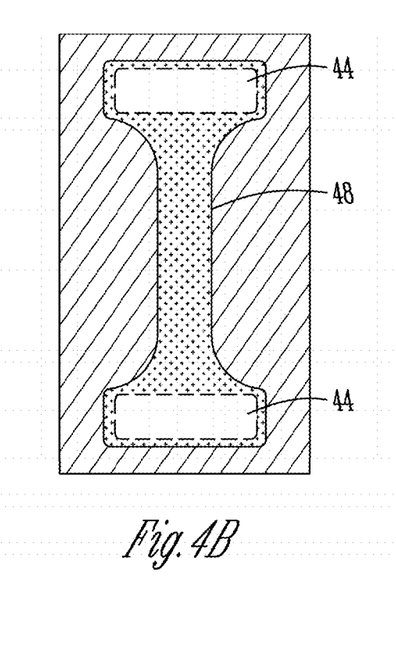
FIG. 4B shows a mold with a 3-day cultured cellular gel.
Figure 4C:
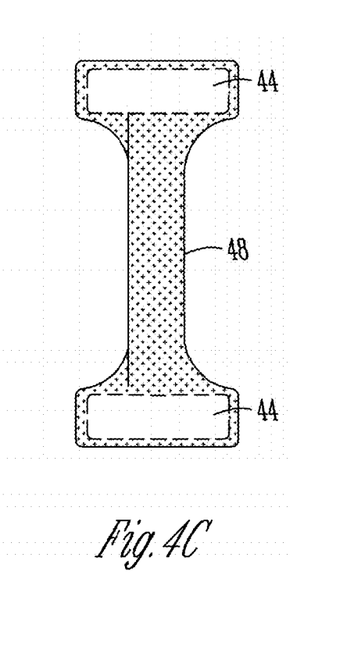
FIG. 4C shows the 3-day cultured cellular gel removed from the mold.

FIG. 2 shows steps for and various illustrations related to preparing a standard silicone mold for a biaxial cellular collagen gel tissue surrogate. The steps comprise providing a cell-suspended solution, mounting the gel and culture for 6 days, allowing the gel in the mold at approximately thirty-seven degrees Celsius and removing the mold and culture for one day.

FIGS. 3A-D and 4A-C show an innovative mold 10 for creating tissue surrogates for mechanobiology research according to some aspects of the disclosure. The design of the mold 10 is typically composed of three components: a machined polytetrafluoroethylene (PTFE) block 12 having cavity 20, a poly lactic acid (PLA) plastic base 26 having a cut-out 34 and a rectangular ridge 36, and a thin PTFE sheet 42. The plastic base 26 is secured to the machined PTFE block 12 using cyanoacrylate. PTFE is preferred for the main material in the mold 10 because PTFE has bio-inert properties (i.e. PTFE will not have an adverse reaction with the cells nor will the cells attempt to attach to PTFE). The PTFE sheet 42 is coated with a thin layer of silicone grease prior to being inserted into the slot created from the interface of the PLA base 26 and the PTFE block 12 in order to prevent fluid leakage through the mold 10.

During preparation of the sample 48, the mold 10 shown in FIGS. 3A-D and 4A-C is only partially filled with a gel or hydrogel to the desired gel thickness, up to forty percent of the height of the mold 10, and the remaining volume of the mold is filled with culture media. The time of cell culture is dependent on the hydrogel, cell type, and goals of the experiment. For example, a prototype mold was tested by creating collagen gel tissue surrogates in the molds that were cultured for three days before being placed into the bioreactor. Alternatively, the gels may sit in the mold 10 for a long period of time such that the mold 10 is used in a static culture setting.

Mechanical constraints 44 may be placed in the ends of the mold 10 to serve as mechanical constraints against cell driven contraction and to be used as a gripping surface in the bioreactor after the gels are removed from the molds. The mechanical constraints 44 are shown in the figures as natural fiber tabs but may be a porous polyethylene bar or any other known material capable of constraining against cell driven contraction.

The design of the mold 10 has multiple advantages over a simple gasket mold. The mold 10 allows each sample 48 to be easily transported because the mold 10 is entirely self-contained. Additionally, the sample 48 can easily eject from the mold 10 by removing the PTFE sheet 42 in the bottom of the PTFE block 12 and applying light pressure to the mechanical constraints 44 at the end of the sample 48. This reduces the risk of damage when transporting the sample 48 to a bioreactor (not shown) after initial gelation. Furthermore, the height of the mold 10 allows samples 48 of varying thicknesses to be created by adjusting the volume of fluid poured into the mold 10. The innovative mold 10 also saves cell culture media because the mold 10 is tall and the remaining volume in the mold can simply be filled with media in the incubator rather than having to fill an entire petri dish to submerge the mold and sample 48. Lastly, while the figures show a mold 10 with a dog-bone geometry, the mold 10 can easily be adapted to any planar gel geometry in the event other research groups require a more complex geometry.

From the foregoing, it can be seen that the present invention accomplishes at least all of the stated objectives.

Non-Limiting Examples of Dimensions

The following list of exemplary dimensions is provided to facilitate an understanding and examination of the present disclosure and the dimensions contained therein are not limiting unless expressly claimed.

The block 12 may have a block height 14 of twenty millimeters, a block width 16 of thirty-three millimeters, and a block length 18 of fifty-seven millimeters. The cavity 20 may have a sample width 22 of seven millimeters and a gauge length 24 of twenty-one millimeters. The base 26 may have a base width 28 of twenty millimeters, a base length 30 identical to the block length 16, and a base height 32 of one and a half millimeters. The ridge or stair 36 may be rectangular and may have a rectangular ridge height 38 of one millimeter and a rectangular ridge width 40 of at least one millimeter. The mechanical constraints 44 may have a mechanical constraint width 46 of twenty-one millimeters.

LIST OF REFERENCE NUMERALS

The following list of reference numerals is provided to facilitate an understanding and examination of the present disclosure and is not exhaustive. Provided it is possible to do so, elements identified by a numeral may be replaced or used in combination with any elements identified by a separate numeral. Additionally, numerals are not limited to the descriptors provided herein and include equivalent structures and other objects possessing the same function.

6 standard silicone mold
7 silicone gasket
8 polypropylene mesh
9 glass plate
10 mold
12 block
14 block width
16 block length
18 block height
20 cavity
22 sample width
24 gauge length
26 base
28 base width
30 base length
32 base height
34 cut-out
36 ridge or stair
38 ridge or stair height
40 ridge or stair width
42 sheet
44 mechanical constraints
46 mechanical constraint width
48 sample The present disclosure is not to be limited to the particular embodiments described herein. The following claims set forth a number of the embodiments of the present disclosure with greater particularity.

What is claimed is:

1. A system for preparing and transporting a cellular or acellular construct for controlled extraction of the construct, the system comprising:
   a sample constructed within a three-dimensional cellular scaffold and culture media;
   a block including a block height of at least twenty millimeters, a block width that is more than the block height, a block length that is more than the block width, a three-dimensional cavity for constructing the sample in three dimensions, wherein the block is made from a bio-inert material that does not produce an adverse effect with said sample, wherein the three-dimensional cavity comprises:
      a cavity height that is identical to the block height,
      a first sub-cavity having a first mechanical constraint,
      a second sub-cavity having a second mechanical constraint,
      a third, elongated sub-cavity, wherein the first sub-cavity and the second sub-cavity are located at each end of the third, elongated sub-cavity, and
      a dog-bone and/or cruciform shape;
   a base including a base height that is less than the block height, wherein the base is made from a bio-inert material; and
   an impermeable, removable sheet inserted into a cutout in the base and slid beneath the block.

2. The system of claim 1, wherein the block is made from polytetrafluoroethylene (PTFE).

3. The system of claim 1, wherein the base is made from poly lactic acid (PLA).

4. The system of claim 1, wherein the impermeable, removable sheet is made from polytetrafluoroethylene (PTFE).

5. The system of claim 1, wherein the impermeable, removable sheet is thinner than the base.

6. The system of claim 1, wherein the impermeable, removable sheet is coated with silicone grease prior to insertion of the impermeable, removable sheet between the block and the base.

7. The system of claim 1, the block width is thirty-three millimeters, and the block length is fifty-seven millimeters.

8. The system of claim 7, wherein the base has a base width identical to the block width, a base length identical to the block length, and the base height is one and a half millimeters.

9. The system of claim 1, wherein the base includes a rectangular cut-out spanning an entire thickness of the base and a rectangular ridge supporting the impermeable, removable sheet.

10. The system of claim 9, wherein the rectangular ridge has a rectangular ridge height of one millimeter and a rectangular ridge width of at least one millimeter.

11. The system of claim 1, wherein the cavity has a sample width of seven millimeters and a gauge length of twenty-one millimeters.

12. The system of claim 1, wherein the first and second mechanical constraints are positioned at each end of the three-dimensional cavity to constrain cell driven contraction and to allow for gripping the sample after the sample is removed from the mold.

13. The system of claim 1, wherein the first constraint and/or the second constraint comprises a natural fiber tab.

14. The system of claim 1, wherein the first constraint and/or the second constraint comprise a porous polyethylene bar.

15. The system of claim 1, wherein the three-dimensional cellular scaffold comprises a collagen gel.

16. The system of claim 15, wherein the sample comprises less than forty percent of the collagen gel and more than sixty percent of the culture media.

17. The system of claim 1, wherein the three-dimensional cellular scaffold comprises fibrin.

18. The system of claim 1, wherein the three-dimensional cellular scaffold comprises agarose.

19. The system of claim 1, wherein the three-dimensional cellular scaffold comprises a hydrogel.

* * * * *